(12) United States Patent
Bergmann et al.

(10) Patent No.: US 7,807,397 B2
(45) Date of Patent: Oct. 5, 2010

(54) DIAGNOSTIC METHOD FOR DISORDERS USING COPEPTIN

(75) Inventors: Andreas Bergmann, Berlin (DE); Joachim Struck, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 316 days.

(21) Appl. No.: 11/573,595

(22) PCT Filed: Aug. 19, 2005

(86) PCT No.: PCT/EP2005/009001

§ 371 (c)(1),
(2), (4) Date: Feb. 12, 2007

(87) PCT Pub. No.: WO2006/018315

PCT Pub. Date: Feb. 23, 2006

(65) Prior Publication Data

US 2009/0221009 A1    Sep. 3, 2009

(30) Foreign Application Priority Data

Aug. 19, 2004    (EP)    ................................. 04019732

(51) Int. Cl.
*G01N 33/00* (2006.01)
*G01N 33/53* (2006.01)
*A61K 38/11* (2006.01)

(52) U.S. Cl. .......................... 435/7.94; 435/7.1; 422/61; 930/150; 530/315

(58) Field of Classification Search ........................ None
See application file for complete search history.

(56) References Cited

U.S. PATENT DOCUMENTS

2004/0253637 A1 * 12/2004 Buechler et al. ............. 435/7.1

FOREIGN PATENT DOCUMENTS

WO    WO 2004/006860    1/2004

OTHER PUBLICATIONS

Seger et al. "The presence and in vivo biosynthesis of fragments of CPP (the C-terminal glycopeptide of the rat vasopressin precursor) in the hypothalamo-neurohypophyseal system" Peptides vol. 8 (1987), 757-762.*
Harlow, E. and Lane, D., Antibodies: A Laboratory Manual (1988) Cold Spring Harbor Laboratory Press, Cold Spring Harbor, NY, pp. 23-24, 72-77, 555-561, 578-582, and 591-592.*
Yamaji et al., "Propressophysin in Human Blood: A Possible Marker of Ectopic Vasopressin Production", Journal of Clinical Endocrinology and Metabolism, vol. 59(3); 1984, 505-512.
Nijenhuis et al., "Familial Neurohypophysial Diabetes Insipidus in a Large Dutch Kindred: Effect of the Onset of Diabetes on Growth in Children and Cell Biological Defects of the Mutant Vasopressin Prohormone", Journal of Clinical Endocrinology and Metabolism, vol. 86(7); 2001, 3410-3420.
Gabreëls et al., "The Vasopressin Precursor Is Not Processed in the Hypothalamus of Wolfram Syndrome Patients with Diabetes Insipidus: Evidence for the Involvement of PC2 and 7B2", Journal of Clinical Endocrinology and Metabolism, vol. 83(11), 1998, 4026-4033.
Nijenhuis et al., "Mutations in the Vasopressin Prohormone Involved in Diabetes Insipidus Impair Endoplasmic Reticulum Export but Not Sorting", The Journal of Biological Chemistry, vol. 274(30), 1999, 21200-21208.
International Search Report for corresponding European Patent application No. EP2005/009001, mailed Nov. 11, 2005.
G. Singh Ranger, "The Physiology and Emerging Roles of Antidiuretic Hormone", Int. J. Clin Pract 2002, vol. 56 (10) 777-782.
Landry et al., "The Pathogenesis of Vasodilatory Shock", The New England Journal of Medicine, vol. 345(8), Aug. 23, 2001, 588-595.
Coates et al., "Differential Cleavage of Provasopressin by the Major Molecular Forms of SPC3", Journal of Neurochemistry, vol. 70(4), 1998, 1670-1678.
Wilson et al., "Elevated Plasma Vasopressin Concentrations During Endotoxin and *E. coli* Shock", Advances in Shock Research, 1981, vol. 6, 15-26.
Landry et al., "Vasopressin Deficiency Contributes to the Vasodilation of Septic Shock", Circulation, 1997, vol. 95(5), 1122-1125.
Sharshar et al., "Depletion of Neurohypophyseal Content of Vasopressin in Septic Shock", Crit Care Med 2002, vol. 30(3), 497-500.
Sharshar et al., "Circulating Vasopressin Levels in Septic Shock", Crit Care Med 2003, vol. 31(6), 1752-1758.
P. Forrest, "Vasopressin and Shock", Anaesthesia and Intensive Care, vol. 29(5), Oct. 2001, 463-472.
J.L. Vincent, "Endocrine Support in the Critically ill", Crit Care Med 30(3), 2002, 702-703.
Holmes et al, "Science Review: Vasopressin and the cardiovascular system part 2-clinical physiology", Crit Care 8, 2004, 15-23.
Lindner et al., "Stress Hormone Response during and after Cardiopulmonary Resuscitation", Anaesthiology 77, 1992; 662-668.
Wenzel et al., "A Comparison of Vasopressin and Epinephrine for Out-of-Hospital Cardiopulmonary Resuscitation", N. Engl. J. Med 350(2), 2004, 105-113.
W.G. North, "Gene Regulation of Vasopressin and Vasopressin Receptors in Cancer", Experimental Physiology, 85 S No. 27S-40S, 2000.

(Continued)

*Primary Examiner*—Gailene R Gabel
*Assistant Examiner*—Christine Foster
(74) *Attorney, Agent, or Firm*—Heslin Rothenberg Farley & Mesiti P.C.

(57) ABSTRACT

The use of copeptin as diagnostic marker for the determination of the release of vasopressin, especially in connection with disorders associated with non-physiological alterations of vasopressin release from the neurohypophysis, especially for detection and early detection, diagnosing and monitoring of the course of cardiovascular diseases, renal and pulmonary diseases as well as shock, including septic shock, sepsis and diseases/disorders of the central nervous system and neurodegenerative diseases.

2 Claims, 4 Drawing Sheets

OTHER PUBLICATIONS

Baumann et al., "Distribution, Blood Transport, and Degradation of Antidiuretic Hormone in Man", The Journal of Clinical Investigation, vol. 57, May 1976, 1109-1116.

Smyth et al., "A New Glycopeptide in Pig, Ox and Sheep Pituitary", Biochemical and Biophysical Research Communications, vol. 87(4), 1979, 1006-1010.

de Bree et al., "Structure-Function Relationships of the Vasopressin Prohormone Domains", Cellular and Molecular Neurobiology, vol. 18(2) 1998, 173-191.

D.A. Holwerda, "A Glycopeptide from the Posterior Lobe of Pig Pituitaries. I. Isolation and Characterization", Eur J. Biochem 28, 1972, 334-339.

Nagy et al., "The Glycopeptide Moiety of Vasopressin-Neurophysin Precursor is Neurohypophysial Prolactin Releasing Factor", Biochemical and Biophysical Research Communications, vol. 151(1), 1988, 524-529.

Hyde et al., "The Vasopressin-associated Glycopeptide is not a Prolactin-Releasing Factor: Studies with Lactating Brattleboro Rats" Endocrinology, vol. 125(1), 1989, 35-40.

W.G. North, "Biosynthesis of Vasopressin and Neurophysins", Vasopressin: Principles and Properties, New York: Plenum Press, 1987, 175-209.

Chesney et al., "Subcellular Localization of Vasopressin-like Material in Platelets", J. Lab. Clin. Med. 1985, vol. 106 (3), 314-318.

Kluge et al., "Improved Extraction Procedure and RIA for Determination of Arginine8-Vasopressin in Plasma: Role of Premeasurement Sample Treatment and Reference Values in Children", Clinical Chemistry vol. 45(1), 1999, 98-103.

Robertson et al., "Development and Clinical Application of a New Method for the Radioimmunoassay of Arginine Vasopressin in Human Plasma", The Journal of Clinical Investigation, vol. 52, Sep. 1973, 2340-2352.

North et al., "Immunohistochemical Evaluation of Vasopressin Expression in Breast Fibrocystic Disease and Ductal Carcinoma In Situ (DCIS)", Endocrine Pathology, 2003, vol. 14(3), 257-262.

North et al., "Vasopressin Gene Related Products are Markers of Human Breast Cancer", Breast Cancer Research and Treatment, vol. 34, 1995, 229-235.

W.G. North, "Neuropeptide Production by Small Cell Carcinoma: Vasopressin and Oxytocin as Plasma Markers of Disease", Journal of Clinical Endocrinology and Metabolism, 1991, vol. 73(6), 1316-1320.

M. Thibonnier, "Vasopressin Receptor Antagonists in Heart Failure" Current Opinion in Pharmacology 2003, vol. 3, 683-687.

* cited by examiner

```
              10         20         30         40         50         60
              |          |          |          |          |          |
     MPDTMLPACF LGLLAFSSAC YFQNCPRGGK RAMSDLELRQ CLPCGPGGKG RCFGPSICCA 70         80         90        100        110        120
              |          |          |          |          |          |
     DELGCFVGTA EALRCQEENY LPSPCQSGQK ACGSGGRCAA FGVCCNDESC VTEPECREGF 130        140        150        160
              |          |          |          |
     HRRARASDRS NATQLDGPAG ALLLRLVQLA GAPEPFEPAQ PDAY
```

1-19      Signal Sequenz
20-28    ARG-VASOPRESSIN.
32-124   NEUROPHYSIN 2.
126-164  COPEPTIN.

FIGURE 3

DIAGNOSTIC METHOD FOR DISORDERS USING COPEPTIN

CROSS REFERENCE TO RELATED APPLICATIONS

This application is a 371 filing of PCT International application no. PCT/EP2005/009001 filed Aug. 19, 2005 and published in English as WO 2006/018315 on Feb. 23, 2006 which claims the priority of European application no. 04019732.9 filed Aug. 19, 2004. The disclosures of these applications and all other patents, published applications and other references cited herein are hereby incorporated by reference in their entirety.

The present invention relates to the use of copeptin and/or its precursors or fragments and/or its splice variants, fragments comprising copeptin and/or combinations and/or derivatives thereof in medical diagnosis as humoral biomarker for disorders associated with or caused by non-physiological alterations of vasopressin release from the neurohypophysis, as there are, for example, cardiac diseases, renal disaeases, inflammatory diseases and sepsis and diseases/disorders of the central nervous system and neurodegenerative diseases and others as mentioned below.

In the following text all biomolecules and fragments, variants and combinations thereof as mentioned above, which share the common feature that they display copeptin immunoreactivity, are referred to as "copeptin" in the present application. The term "copeptin", therefore, inter alia also comprises for example VP-prohormone, if present in a sample as such.

Copeptin according to the present invention is used as biomarker, especially humoral biomarker, which can be used to diagnose disorders associated with or caused by non-physiological alterations, espcially increases, of vasopressin release from the neurohypophysis as there are cardiovascular diseases like chronic or congestive heart failure, cardiac arrest, cardiac shock, cardiac infarction, acute myocardial infarction, arterial hypertension, cardiac surgery, cirrhosis, pulmonary disorders, kidney (renal) diseases as polycystic kidney disease, Diabetes insipidus, forms of hyponatremia, forms of syndrome of inappropriate antidiuretic hormone secretion, hemorrhage, edema-forming states, inflammatory diseases, trauma, burns, infectious complications thereof and sepsis, severe sepsis and septic shock, as well as diseases/disorders of the central nervous system (CNS) and neurodegenerative diseases.

If, in the present application, a use as biomarker is mentioned, this means the determination of said biomarker in in vitro samples of biological fluids (i.e. ex vivo) as-blood, serum or plasma and liquor cerebrospinalis (cerebrospinal fluid; CSF). For any skilled person this clearly implies that only such physiologically occurring "copeptin" molecules are to be determined which in fact can be present in such samples. There may be present in a sample of a body fluid several distinct species of essentially identical immunoreactivity, which differ e.g. in length and/or by the presence and/or type and/or degree of their posttranslational modification, e.g. glycosylation and/or phosphorylation. In view of the inherent possibility that any given assay may recognize more than just one sort of molecule, according to a preferred embodiment the determination of copeptin is to be understood as determination of copeptin immunoreactivity, especially preferred as immunoreactivity as measured with an assay as described below.

As far as the use of the present invention also extends to the preparation of assay components and reagents useful in connection with the determination of copeptin as biomarker, or as active ingredient in pharmaceuticals, any suitable copeptin peptides or derivatives, including fusion products and modifications having e.g. a reduced homology with the naturally occurring copeptin, or having a modified stability, can be used, without any restriction to naturally occurring copeptin products.

The term copeptin of the present invention consequently comprises also amino acid sequences showing e.g. only 75% homology, preferred at least 80% homology, more preferred at least 90% homology to copeptin.

Terms as "diagnosis" or "diagnostic" are used in this specification as general terms, which, if not defined otherwise, are intended to comprise not only diagnosis in the sense of identifying a specific disease, but also screening of asymptomatic or high risk populations at risk of certain diseases or suspected to have certain diseases, especially for early detection, monitoring of untreated or treated patients and monitoring the course of a therapy and for prognosis/early prognosis and survival prognosis.

The invention further relates to antibodies raised against copeptin or against partial peptides of copeptin, especially for use in a method as mentioned above, as well as kits and assays involving such components.

Vasodilatory states of shock are life threatening situations. The peripheral blood pressure decreases drastically and often does not normalise after administration of catecholamines. The most frequent form of shock is septic shock, which is also the most severe form of sepsis. Furthermore vasodilatory shock can manifest itself after severe heart surgery, hemorrhagic and cardiac shock or after poisoning by medicaments or toxins [1, 2].

A series of peptides being predominantly effective via the autocrine/paracrine route are involved in the regulation of blood pressure. The following molecules are known to have vasodilatory function: e.g. adrenomedullin, calcitonin gene-related peptide (CGRP) and atrial natriuretic peptide (ANP). Vasoconstrictive effects show for example the following molecules: endothelin, angiotensin II and vasopressin (also known as arginine-vasopressin, antidiuretic hormone (ADH)).

Vasopressin is a cleavage product of a larger precursor molecule ("VP pro-hormone"; its polypeptide sequence is shown in FIG. 3; or as SEQ ID NO:4) that is mainly formed in the neurons of the hypothalamus [20]. After synthesis the VP pro-hormone is glycosylated in the Golgi apparatus, packed into secretory vesicles and split by pro-hormone convertase SP3 into the three peptides vasopressin, neurophysin and copeptin. After axonal migration to the nerve endings of the hypophysis the peptides are secreted from the vesicles upon certain stimuli (e.g. high osmolarity, decrease of blood volume or different hormones).

The most prominent physiological effect of vasopressin is the retention of body water (antidiuresis). The effect of vasopressin to physiologically increase blood pressure is in healthy individuals less prominent than in septic shock. Further physiological functions of vasopressin are the regulation of the pituitary adrenal axis (ACTH, Cortisol), stimulation of the activity of the gastro-intestinal tract and the aggregation of blood platelets [1; numbers in brakkets refer to the attached list of literature references].

In the pathogenesis of shock vasopressin plays a central role: in experimental shock-models it was shown that plasma concentrations of vasopressin are increased by three orders of magnitude above the normal concentration within 15 minutes after stimulation [4]. After rapid release of vasopressin stored in the hypophysis the vasopressin concentrations are decreasing drastically during further course of shock syndrome as was observed in patients with septic shock [5-7]. This observation was the base for the concept of a vasopressin substitution therapy for the treatment of septic shock that was successfully tested [8-10]. These results indicate that an endogenous decrease of vasopressin is contributing to the state of septic shock [5].

Vasopressin has also been discussed as a marker for the prognosis of probability of survival of patients with cardiac arrest [11] and consequently it was used for the treatment of such patients [12].

A pathophysiological overexpression of vasopressin or VP pro-hormone has been shown for several types of cancer like prostate, testicular cancer, ovarian and pancreatic cancer, pituitary adenomas and gangliomas, olfactory neuroblastomas, breast and colon tumours, nasopharyngeal carcinoma, head and neck cancer, phaeochromocytoma and tumours of gastrointestinal origin, squamous-cell carcinomas, adenocarcinomas and large cell carcinomas [13, 24, 25, 26]. Vasopressin produced or released in cancers is to be considered as pathophysiologically formed, i.e. formed by unnormal physiological routes (altered pathological tissues) which are distinct from the normal physiological vasopressin production.

In diseases as mentioned above vasopressin is released from an organ (neurohypophysis) which is its normal origin, although in non-physiological levels.

Copeptin—also known as C-terminal glycoprotein—comprises 39 amino acids, its sugar moiety and has a molecular weight of about 2000 Da [15-17]. The glycosylation is at position, 131 of the precursor VP-prohormone (cf. SEQ ID NO:4). The biological function of copeptin remains unclear.

The direct determination of vasopressin as humoral diagnostic marker in body fluids as e.g. serum or plasma itself is not suitable for routine diagnostics. More than 90% of vasopressin are bound to blood platelets and are thus not available for the measurements [21]. Thus free vasopressin found in the plasma does not reflect the true amount of vasopressin released into the blood stream. The binding of vasopressin to the blood platelets leads to different results, depending on the amount of platelets included in the measurement, which is variable depending on the centrifugation used to obtain the plasma [22]. A further hindrance is the fact that a higher amount of vasopressin is observed, if the blood sample is left at room temperature before centrifugation. These effects and the short half-life of vasopressin in vivo (24 minutes, [14]) and in plasma samples ex vivo even when stored at −20 [23] so far has hindered the use of vasopressin in routine diagnostics. Due to the short half-life, it is not possible in routine diagnostics to take samples, obtain the plasma, transport the sample into the laboratory and do the diagnostics in the laboratory including the required tests before vasopressin reaches a critical level of detection.

Furthermore due to the low in vivo stability of vasopressin and the variable results due to the binding to and release from blood platelets, the use as a biomarker is extremely limited even under optimized samples logistics, as the influence of the degradation occurs rapidly.

The object of the invention was to overcome the effects of the disadvantageous half-life of vasopressin and the variable results in measurements and to develop a method, use and a kit for the detection and determination of the molecules associated with the release of vasopressin, more specially copeptin, for the diagnosis of cardiovascular diseases and sepsis.

This object could be achieved on the basis of the surprising finding that certain fragments of VP prohormone—the precursor of vasopressin—copeptin in particular, can be used as a tool for the determination of the physiological release of vasopressin, in particular in body fluids, in the diagnosis and monitoring of cardiovascualr diseases and sepsis.

This generation of the fragments, copeptin in particular, correlates with the release of vasopressin, since all are derived from the same precursor.

Furthermore the stability of the precursor proteins, fragments and/or combinations thereof ex vivo were found to be surprisingly high and render the fragments, copeptin in particular, fully suitable for routine purposes.

This linkage between the fragments like copeptin and other fragments of the precursor peptides made them suitable as diagnostic tools for all diseases, where vasopressin plays a role. Copeptin in particular can therefore be used in mediacal diagnostics for diagnosing and monitoring a variety of diseases, especially cardiovascular diseases and systemic inflammations, especially sepsis.

Furthermore the present invention in one embodiment relates to the use of copeptin for diagnosis of the diseases, course control and prognosis for the above mentioned diseases where vasopressin plays a role.

Clinical data may additionally be taken into consideration to support the determination of the disease.

It is possible to use amino acid sequences showing at least 75% homology, preferred 80% homology more preferred at least 90% homology to copeptin according to the present invention.

In a preferred embodiment of the present invention according to the following examples two regions (PATV17; PLAY17) of the human vasopressin-neurophysin 2-copeptin-precursor amino acid sequence were chosen as immunological binding sites to be recognized by specific antibodies:

```
positions 132-147:
CATQLDGPAGALLLRLV              (PATV17 - SEQ ID
                                NO:1)

positions 149-164:
CLAGAPEPFEPAQPDAY,             (PLAY17 - SEQ ID
                                NO:2)
```

For calibration purposes and for the preparation of standard solutions, a peptide comprising both binding sites mentioned above was used (PAY33):

```
positions 132-164:
                               (PAY33 - SEQ ID NO:3)
ATQLDGPAGALLLRLVQLAGAPEPFEPAQPDAY.
```

The immunological binding sites PATV17 and PLAY17 to be recognized by specific antibodies were selected such that they do not include the putative glycosylation site of copeptin at position 131. Therefore, the presence or absence of a post-translational modification (glycosylation) of the determined copeptin should not have any significant impact on the recognition of copeptin in an assay using such antibodies. The term "copeptin", therefore, includes the "naked" copeptin peptide as well as posttranslationally modified forms of said peptide.

When each of the peptides mentioned above was synthesized as described below, an amino terminal cysteine residue was added to each copeptin amino acid sequence, and the peptides were chemically synthesized as soluble proteins according to methods known by the person skilled in the art. They were purified and quality controlled by mass spectroscopy and reversed phase HPLC and lyophilized into aliquots (Jerini A G, Berlin, Germany).

The synthesized peptides according to the present invention were used to produce antigens and injected into animals to raise antibodies against copeptin according to the present invention. Different methods can be used to achieve this object known by the person skilled in the art.

In a preferred embodiment the peptides PATV17 and PLAY17 were conjugated to a carrier protein keyhole limpet hemocyanin (KLH) via MBS (m-maleimidobenzoyl-N-hydroxysuccinimide ester) according to the methods of Pierce, Rockford, Ill., USA. Antibodies were produced to the above mentioned peptides in sheep. In a preferred embodiment of the present invention, polyclonal antibodies were raised against the above mentioned peptides. Antibodies were purified according to known methods. In a preferred embodiment of the invention, this was achieved preferably by ligand specific affinity chromatography by coupling the peptides via the amino terminal cystein residue to SulfoLink-Gel of Pierce (Boston, USA) according to the methods of Pierce. In a preferred embodiment the antibodies were tagged with a marker to enable detection. The marker used is preferably a luminescent marker and in a yet more preferred embodiment, the antibody was tagged with a chemiluminescent marker and in a yet further preferred embodiment the antibodies against PATV17 (0413-pAK) and PLAY17 (0417-pAK) were tagged with a chemiluminescent marker.

The invention in a further preferred embodiment involves the use of the generated antibodies for detection of copeptin in accordance with the present invention in samples of body fluids, as well as a kit comprising a certain quantity of such an antibody or more antibodies specific to detect molecules in accordance with the present invention. Different assays can be used to detect the molecules as are known to the person skilled in the art comprising competitive or sandwich immunoassays in manual, automated or point of care test formats employing various kinds of labels.

Methods for the detection of binding of the antibody to the respective molecule are also known by the person skilled in the art. All such known assay formats can be used in the context of the determination of copeptin. It is, for example, within the scope of the present invention to determine copeptin with the aid of a rapid test device, e.g. of the immunochromatographic type, as so-called POC (Point of Care) test. The determination of copeptin can also be conducted with a homogeneous assay of the so-called KRYPTOR® type, using the so-called TRACE® technology.

A preferred embodiment of the present invention discloses the use of antibodies generated against the above mentioned peptides, 0413-pAK and 0417-pAK, in particular for a two-site immunoassay of the sandwich type. Another preferred embodiment of the invention discloses the use of these antibodies for the detection and the determination of the concentration of the molecules of the present invention, copeptin in particular in various body fluids and other biomaterials. In a preferred embodiment copeptin can be detected at concentrations above 50 pg/ml of body fluid (FIG. 1).

In one embodiment the invention is based on and uses the discovered long term stability of copeptin ex vivo in plasma and serum (Table 2). In plasma and serum copeptin levels were surprisingly stable even after two days storage at room temperature. Thus copeptin is by far more suitable for diagnostic purposes than vasopressin.

A preferred embodiment of the invention discloses the use of antibodies generated against PLAY17 and PATV17 for the detection of copeptin in healthy individuals, in patients with sepsis, cardiac infarction and-increased arterial blood pressure (FIG. 2), and for determining the severity of chronic or congestive heart failure (CHF) (FIG. 4).

The invention further permits the determination of the presence and stability of the molecules of the present invention, copeptin in particular in body fluids, and the determination of the difference in peptide concentration in healthy controls and patients of various diseases comprising those mentioned above (FIG. 2; FIG. 4). The median of healthy control individuals is at about 13 pg/ml.

The invention further discloses a significant change of the concentration of the humoral biomarker copeptin in body fluids in state of disease comprising those mentioned above.

A preferred embodiment of the invention is based on the surprising finding of a highly significant change i.e. an about 10 fold increase in copeptin concentration in plasma of sepsis patients (median 150.5 pg/ml) and in cardiac infarction (median 129.5 pg/ml) and an about 35 fold increase in patients with increased arterial blood pressure (median 459.5 pg/ml).

In patients with CHF the measured levels of copeptin correlates well with the severity of the illness which is generally evaluated using the New York Heart Association (NYHA) functional classification system, wherein NYHA classes I to IV correspond to the following typical functional capacities: NYHA class I—asymptomatic; NYHA class II—symptoms with moderate exertion; NYHA class III—symptoms with minimal exertion; NYHA class IV—symptoms (dyspnea) at rest. In a study in which copeptin levels in plasma samples of a total of 348 CHF patients (25 in NYHA class I; 124 in NYHA class II; 127 in NYHA class III; 72 in NYHA class IV; see Table 1) were determined, the medians for the different classes showed a clear tendency (see Table 1 below).

The invention also provides a diagnostic method, kit and assay for the above mentioned diseases, using one or more antibodies of copeptin in particular.

DESCRIPTION OF THE FIGURES

FIG. 3 shows the vasopressin prohormone amino acid sequence (one-letter code; cf. also SEQ ID NO:4).

MATERIALS, METHODS AND MEASUREMENTS

EXAMPLE 1

Peptide Synthesis

Figure 1:
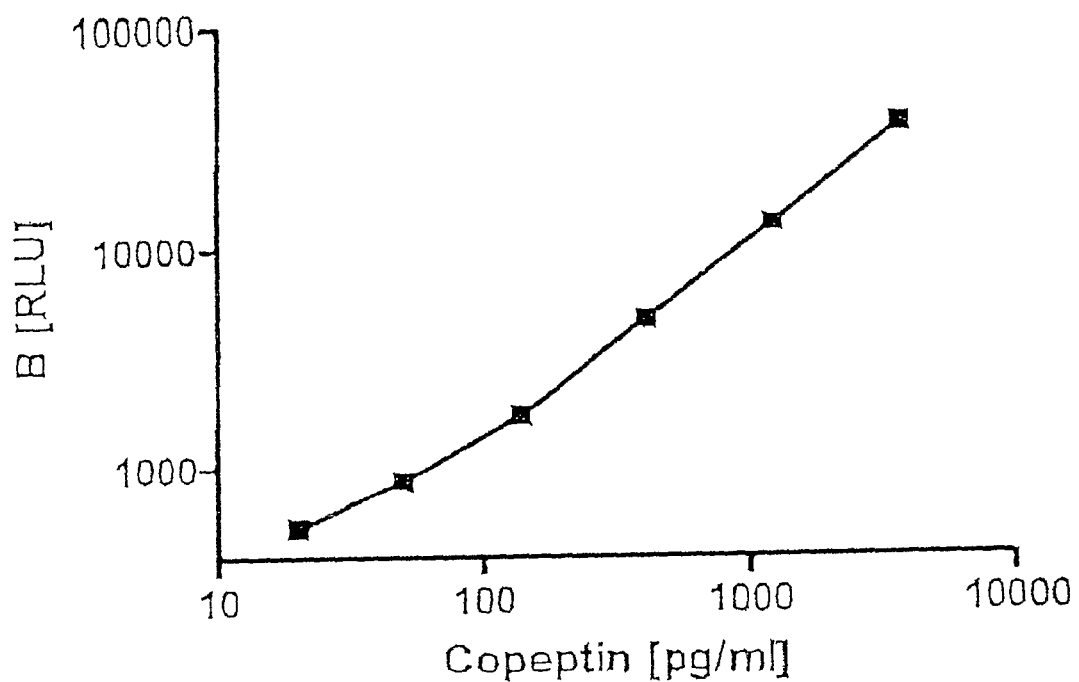
FIG. 1 shows the standard curve for the sandwich-immunoassay for copeptin immunoreactivity using the peptide PAY33 as a standard material.

Peptides were synthesized and their quality was controlled by mass spectrometry and reversed phase HPLC and lyophilised in aliquots (Jerini AG, Berlin, Germany) according to standard procedures known to the person skilled in the art. The amino acid sequences of the peptides are the following (numbers refer to corresponding positions in the human provasopressin-neurophysin 2-copeptin-precursors (positions 132-147 and 149-164):

```
PATV 17 (132-147 + N-terminal cystein residue):
CATQLDGPAGALLLRLV,                  [Sequence ID 1]

PLAY 17 (149-164 + N-terminal cystein residue):
CLAGAPEPFEPAQPDAY,                  [Sequence ID 2]
```

```
Standard peptide PAY 33 (132-164)
ATQLDGPAGALLLRLVQLAGAPEPFEPAQPDAY. [Sequence ID 3]
```

EXAMPLE 2

Conjugation and Immunization

Peptides of Sequence IDs 1-2 were conjugated to the carrier protein KLH (keyhole limpet hemocyanin) by MBS (-Maleimidobenzoyl-N-hydroxysuccinimid ester) according to the protocols for "NHS-esters-maleimide crosslinkers" by PIERCE, Rockford, Ill., USA. Sheep were immunized receiving 100 µg of conjugate (µg according to the peptide content of the conjugate) and subsequently 50 µg of conjugate every four weeks (quantitiy related to the peptide content of the conjugate). Starting at month 4 after immunization every four weeks 700 ml of blood were withdrawn from every sheep and antiserum was gained by centrifugation. Conjugation, immunizations and production of antisera were done by MicroPharm, Carmerthenshire, UK.

EXAMPLE 3

Purification of Antibodies

The polyclonal antibodies from sheep were purified using ligand specific affinity purification. For that step the peptides PATV 17 and Play 17 were linked to SULFOLINK-GEL® supplied by Pierce (Boston, Mass. USA). The binding occurred according to the protocol of the manufacturer. 5 mg of peptide were added per 5 ml of gel.

In summary, columns were washed three times with 10 ml elution buffer (50 mM citric acid, pH 2.2) and binding buffer (100 mM sodium phosphate, 0.1% Tween, pH 6.8). 100 ml of sheep antiserum were filtered using a filter diameter of 0.2 µm and added to the column material, which had been transferred from the column to a beaker with 10 ml binding buffer. The material was incubated over night at room temperature, by gentle rotation. The material was transferred to empty columns (NAP®-25, Pharmacia, emptied). The eluates were discarded. Subsequently the columns were washed with 250 ml protein-free binding buffer (protein content of washed eluate <0.02 A 280 nm): Elution buffer was added to the washed columns and fractions of 1 ml were collected. The protein content of each fraction was determined by the BCA-method (according to the protocol of PIERCE, Rockford, Ill. USA). Fractions of a protein content >0.8 mg/ml were pooled. After determination of protein content 39 mg of anti-PATV 17 antibody 0413-pAk and 103 mg of anti-PLAY 17 antibody 0417-pAk were gained.

EXAMPLE 4

Tagging

The anti-PLAY 17 antibody 0417-pAk was treated as follows:

500 µl of affinity purified antibodies generated were rebuffered in 1 ml 100 mM potassium phosphate buffer (pH 8.0) via a gel filtration column (NAP-5®, commercially available from Pharmacia) according to the protocol of Pharmacia. The protein concentration of antibody solution was 1.5 mg/ml.

For the tagging with a chemiluminescent marker 10 µl of MA70-Akridinium-NHS-ester (1mg/ml; Hoechst Behring) were added to 67 µl of antibody solution and incubated for 15 minutes at room temperature. Then 423 µl of 1 M glycine was added and incubated for 10 minutes. The solution was rebuffered in 1 ml solvent A (50 mM potassium phosphate, 100 mM NaCl, pH 7.4) using a NAP-5®gel filtration column according to the protocols of Pharmacia. For final elimination of unbound label a gel filtration HPLC was done (Column: Waters Protein Pak SW300). The sample was added and chromatographed at a flow rate of 1 ml/minute in solvent A. The flow was continuously monitored in a UV-meter at wave length of 280 and 368 nm to determine the degree of tagging. The absorption ratio 368/280 nm of labelled antibody was 0.1. The fractions containing monomeric antibodies were collected (retention time 8-10 minutes) and taken up in 3 ml 100 mM sodium phosphate, 150 mM NaCl, 5% bovine serum albumin, 0.1% sodium azide, pH 7.4)

EXAMPLE 5

Coupling

The anti-PATV 17 antibody 0413-pAk was immobilized on irradiated 5 ml polystyrol tubes (Greiner, Germany). For that procedure the antibody solution was diluted to a protein concentration of 6.6 µg/ml with 50 mM Tris, 100 mM NaCl, pH 7.8. 300 µl of diluted protein solution per tube were pipetted. These were incubated for 20 hours at 22° C., the solution was removed. Then 4.2 ml of a 10 mM sodium phosphate, 2% Karion FP, 0.3% bovine serum albumin, pH 6.5 solution were added to each tube. After 20 hours the solution was removed and the tubes were dried in a vacuum drier.

EXAMPLE 6

Immunoassay

The following assay buffer was used: 100 mM sodium phosphate, 150 mM NaCl, 5% bovine serum albumin, 0.1% unspecified sheep IgG, 0.1% sodium azide, pH 7.4.

The copeptin concentration of EDTA-plasma of healthy individuals and patients of various diseases/diseases mentioned above was determined, heart diseases and diseases of the circulation in particular.

As a standard material chemically synthesized peptide (peptide PAY 33) was used which corresponds to positions 132-164 of vasopressin-neurophysin 2-copeptin precursor. The standard was diluted in normal horse serum (Sigma). B5,AMD In the test tubes 100 µl of standards or sample as well as 100 µl of assay buffer was pipetted. The tubes were incubated for two hours at 22° C. using gentle rotation. After washing 4 times with 1 ml of washing buffer (0.1% Tween 20), the supernatant was discarded. Then 200 µl of assay buffer, containing 1 million RLU (relative light units) of MA70-tagged antibody was added and incubated for a further two hours under gentle rotation at 22° C. After washing 4 times with 1 ml of washing buffer (0.1% Tween 20), the chemiluminescence bound to the tube was determined in a luminometer (Berthold, LB952T, basic reagents Brahms AG).

Using the software MULTICALC® (Spline Fit), the concentrations of the samples were determined.

EXAMPLE 7

Determination of Copeptin Concentration

The term copeptin immunoreactivity describes the amount of substrate detected by the developed sandwich immunoassay. The sandwich immunoassay uses antibodies raised against positions 132-147 and 149-164 of the vasopressin-neurophysin 2-copeptin-precursor for detection of the substrate. A typical standard curve for the developed assay is described in FIG. 1. Using the assay concentrations above 50 pg/ml copeptin immunoreactivity in plasma or serum can be determined quantitatively.

EXAMPLE 8

Figure 2:
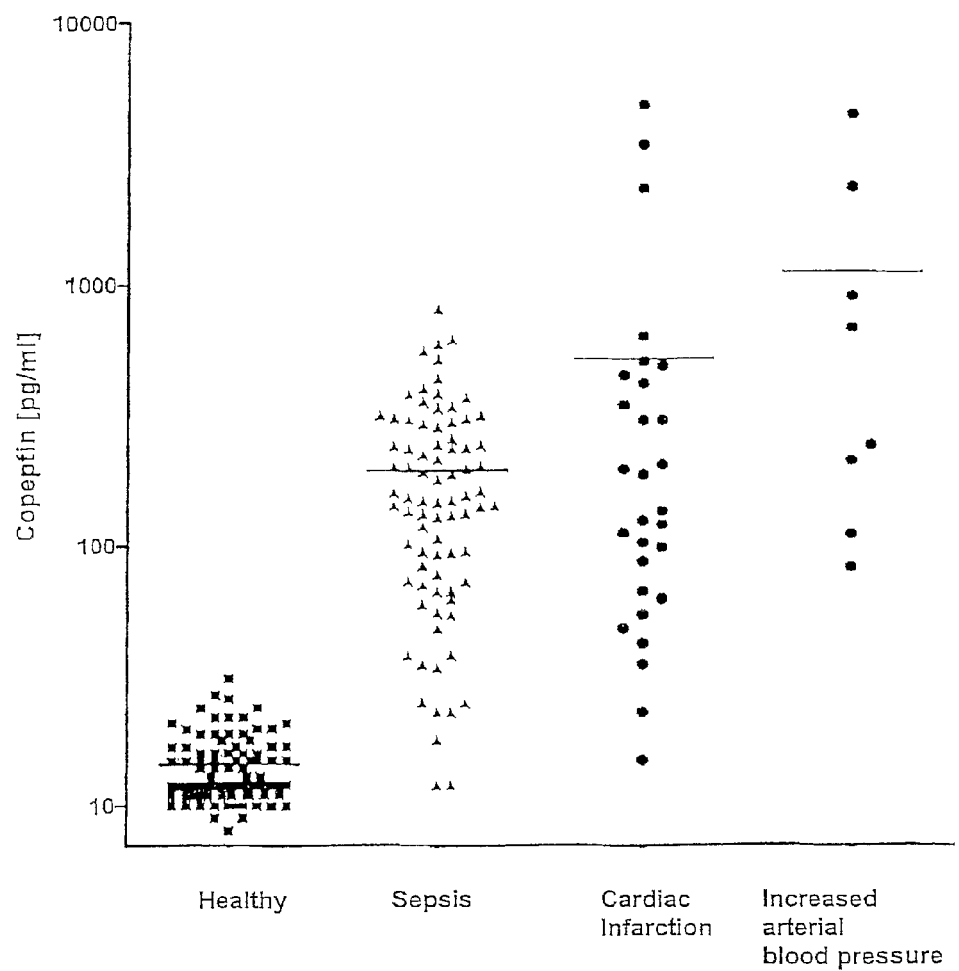
FIG. 2 shows the concentration of copeptin immunoreactivity in samples of healthy individuals and different groups of patients (sepsis, cardiac infarction and increased arterial blood pressure).

Concentration of Copeptin Immunoreactivity in Healthy Individuals and State of Disease Serum and plasma of healthy individuals and patients suffering from various diseases comprising sepsis, cardiac infarction and increased arterial blood pressure were analysed (FIG. 2): The copeptin immunoreactivity was determined. Compared to healthy individuals copeptin immunoreactivity was surprisingly increased in state of disease. Healthy individuals showed a median of about 13 pg/ml, sepsis patients a median of about 150 pg/ml, in cardiac infarction the median was about 129 pg/ml and in increased arterial blood pressure the median was about 459 pg/ml.

EXAMPLE 9

Figure 4:
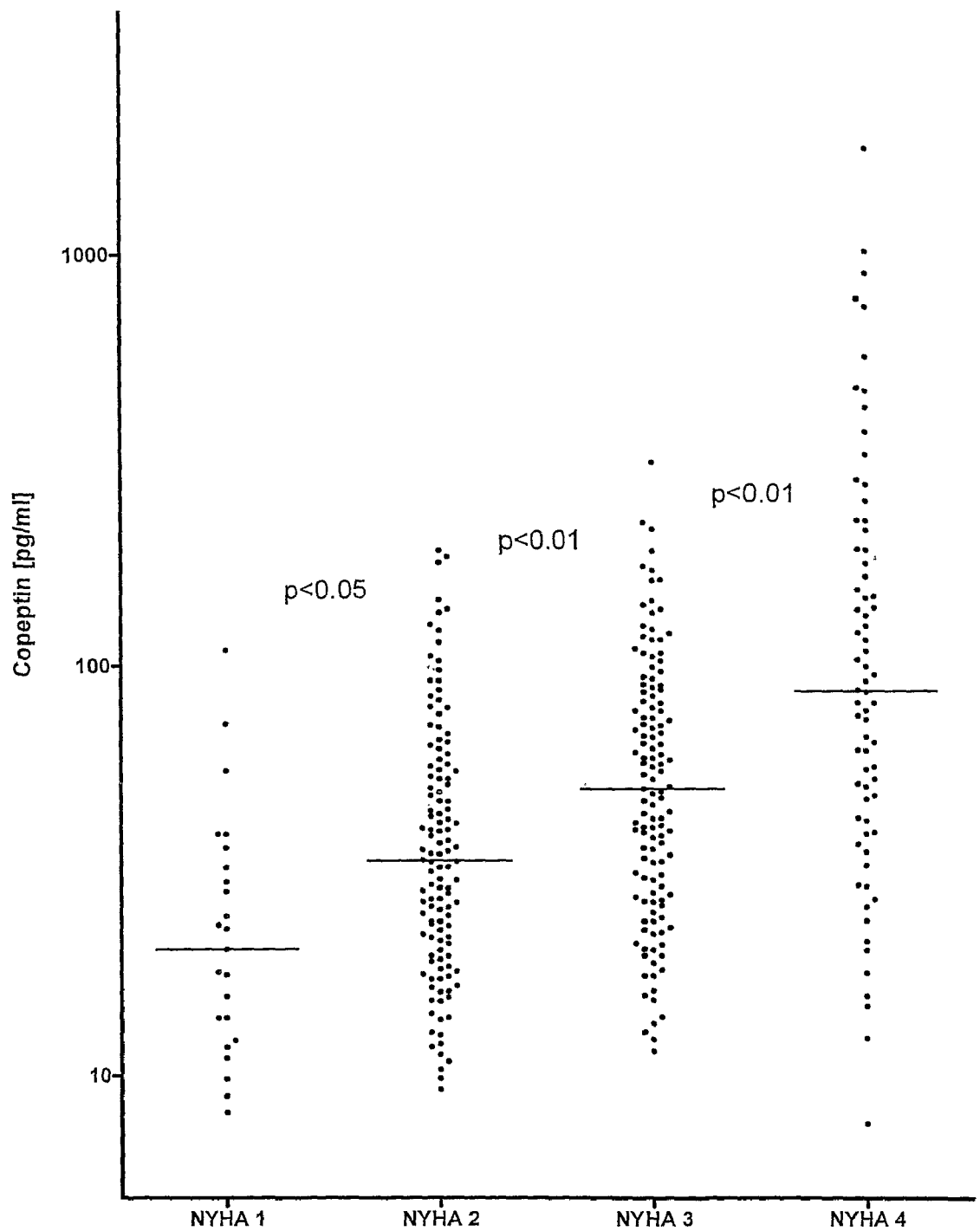
FIG. 4 shows the concentrations of copeptin immunoreactivity in samples of patients with CHF (chronic heart failure) classified according to the NYHA classification system.

Concentration of Copeptin Immunoreactivity in Patients With Chronic Heart Failure (CHF) of NYHA Classes I to IV In serum and plasma samples of a total of 348 CHF patients (25 in NYHA class I; 124 in NYHA class II; 127 in NYHA class III; 72 in NYHA class IV; see Table 1) copeptin levels were determined using the assay described above. The results are shown in diagrammatic form in FIG. 4. As can be seen, the medians of the copeptin concentration in pg/ml for the different classes showed a clear tendency to increase in that the median for patients of NYHA class I was found to be 20.30 pg/ml, class II 33.25 pg/ml, class III 49.60 pg/ml, and class IV 85.80 pg/ml (see the statistical data in Table 1 below).

TABLE 1

|  | NYHA I | NYHA II | NYHA III | NYHA IV |
|---|---|---|---|---|
| Number of values | 25 | 124 | 127 | 72 |
| Median | 20.30 | 33.25 | 49.60 | 85.80 |
| Mean | 27.00 | 45.32 | 63.91 | 184.7 |
| Lower 95% CI of mean | 17.45 | 38.79 | 55.29 | 118.9 |
| Upper 95% CI of mean | 36.56 | 51.86 | 72.54 | 250.5 |

CI = confidence interval

The finding that there is a close correlation of the severity of CHF with the copeptin levels in plasma makes copeptin a biomarker candidate for use in the diagnosis (positive or negative diagnosis) of CHF, the monitoring of the course and evolution of CHF and the monitoring and control of a CHF therapy. Further, in view of current attempts to evaluate the usefulness of vasoporessin receptor antagonists in the therapy of heart failure [27], the determination of copeptin in serum or plasma samples of heart failure patients can allow the identification of such patients who would benefit more than others from a treatment with vasopressin receptor antagonists.

EXAMPLE 10

Stability of Copeptin Immunoreactivity

Copeptin immunoreactivity was found to be surprisingly stable in plasma and serum (Table 2). Table 2 shows the ex vivo stability of endogenous immunoreactive copeptin in serum and plasma of sepsis patients.

TABLE 2

| Sample | Storage (days/temperature) | Recovery (%) |
|---|---|---|
| Serum (n = 3) | 1 d/4° C. | 98.0% |
|  | 2 d/4° C. | 99.2% |
|  | 1 d/RT | 94.1% |
|  | 2 d/RT | 103.7% |
| Plasma (n = 5) | 1 d/4° C. | 103.4% |
|  | 2 d/4° C. | 101.6% |
|  | 1 d/RT | 99.9% |
|  | 2 d/RT | 104.9% |

Even after two days storage at room temperature (RT) no decrease in immunoreactivity could be detected.

Thus the ex vivo stability of copeptin immunoreactivity is surprisingly remarkably increased as compared to vasopressin.

LITERATURE

1. Singh Ranger G: The physiology and emerging roles of antidiuretic hormone. Int. J. Clin. Pract. 56:777-782, 2002;
2. Landry D W, Oliver J A: The pathogenesis of vasodilatory shock. N. Engl. J. Med. 345:588-595;
3. Coates L C, Birch N P: Differential cleavage of provasopressin by the major molecular forms of SPC3. J. Neurochem. 70:1670-1678, 1998;
4. Wilson M F, Brackett D J, Tompkins P, Benjamin B, Archer L T, Hinshaw L B: Elevated plasma vasopressin concentrations during endotoxin and E. coli shock. Adv. Shock. Res. 6:15-26, 1981;
5. Landry D W, Levin H R, Gallant E M, Ashton R C, Jr., Seo S, D'Alessandro D, Oz M C, Oliver J A: Vasopressin deficiency contributes to the vasodilation of septic shock. Crit. Care Med. 30:497-500;
6. Sharshar T, Carlier R, Blanchard A, Paillard M, Raphael J C, Gajdos P, Annane D: Depletion of neurohypophyseal content of vasopressin in septic shock. Crit Care Med 30:497-500, 2002;
7. Sharshar T, Blanchard A, Paillard M, Raphael J C, Gajdos P, Annane D: Circulating vasopressin levels in septic shock. Crit Care Med 31:1752-1758, 2003;
8. Forrest P: Vasopressin and shock. Anaesth Intensive Care 29:463-472, 2001;
9. Vincent J L: Endocrine support in the critically ill. Crit Care Med 30:702-703, 2002;
10. Holmes C L, Landry D W, Granton J T: Science Review: Vasopressin and the cardiovascular system part 2-clinical physiology. Crit Care 8:15-23, 2004;
11. Lindner K H, Strohmenger H U, Ensinger H, Hetzel W D, Ahnefeld F W, Georgieff M: Stress hormone response during and after cardiopulmonary resuscitation. Anaesthiology 77:662-668, 1992;
12. Wenzel V, Krismer A C, Arntz H R, Sitter H, Stadlbauer K H, Lindner K H: A comparison of vasopressin and epinephrine for out-of-hospital cardiopulmonary resuscitation. N Engl J Med 350:105-113, 2004;
13. North W G: Gene regulation of vasopressin and vasopressin receptors in cancer. Exp Physiol 85 Spec No: 27 S-40 S, 2000;
14. Baumann G, Dingmann J F: Distribution, blood transport and degradation of antidiuretic hormone in man. J Clin Invest 57:1109-1116, 1976;
15. Smyth D G, Massey D E: A new glycopeptide in pig, ox and sheep pituitary. Biochem Biophys Res Commun 87:1006-1010, 1979;

16. de Bree F M, Burbach J P: Structure-function relationships of the vasopressin prohormone domains. Cell Mol Neurobiol 18:173-191, 1998;
17. Holwerda D A: A glycopeptide from the posterior lobe of pituitaries. I. Isolation and characterization. Eur J Biochem 28:334-339, 1972;
18. Nagy G, Mulchahey J J, Smyth D G, Neill J D: The glycopeptide moiety of vasopressin-neurophysin precursor is neurohypophysial prolactin releasing factor. Biochem Biophys Pes Commun 151:524-529, 1988;
19. Hyde J F, North W G, Ben-Jonathan N: The vasopressin-associated glycopeptide is not a prolactin-releasing factor: studies with lactating Brattleboro rats. Endocrinology 124: 35-40, 1989;
20. North, W. G. "Biosynthesis of vasopressin and neurophysins" in: D. Gash and G. Boer (eds.), Vasopressin: Principles and Properties, pp. 175-209. New York: Plenum Press, 1987);
21. Chesney et al., J. Lab. Clin. Med. 1985, S. 106, abruf-bar unter www.ncbi.nih,qov;
22. Kluge et al., Clinical Chemistry 1999, S. 98-100
23. Robertson et al., Journal of Clinical Investigation, Vol. 52, 1973, S. 2340-2352;
24. North, W. G. et al, "Immunohistochemical Evaluation of Vasopressin Expression in Breast Fibrocystic Disease and Ductal Carcinoma In Situ (DCIS)", Endocrine Pathology, 2003, Vol. 14, No. 3, 2003, pages 257-262;
25. North W. G. et al., "Vasopressin gene related products are markers of human breast cancer". Breast Cancer Research and Treatment, Vol. 34, 1995, pages 229-235;
26. North W. G.: "Neuropeptide Production by Small Cell Carcinoma: Vasopressin and Oxytocin as Plasma Markers of Disease", J Clin Endocrinol Metab, Vol. 73, 1991, No. 6, pages 1316-1320;
27. Thibonnier M., Vasopressin receptor antagonists in heart failure, Current Opinion in Pharmacology 2003, 3:683-687.

The invention claimed is:

1. A kit for determining the amount of copeptin in a bodily fluid sample, wherein said kit comprises:
   (a) a first antibody that specifically binds a first epitope on a first peptide consisting of amino acids 132-147 of SEQ ID NO.:4,
   (b) a second antibody that specifically binds to a second epitope on a second peptide consisting of amino acids 149-164 of SEQ ID NO.: 4; wherein at least one of said first or second antibodies carries a detectable label; and
   (c) a calibrator peptide consisting of the amino acid sequence of SEQ ID NO.: 3.

2. The kit of claim 1, wherein said bodily fluid sample is blood, plasma or serum.

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Artificial
<220> FEATURE:
<221> NAME/KEY: misc_feature
<222> LOCATION: 1..16
<223> OTHER INFORMATION: Synthetic peptide

<400> SEQUENCE: 1

Cys Ala Thr Gln Leu Asp Gly Pro Ala Gly Ala Leu Leu Leu Arg Leu
1               5                   10                  15

Val

<210> SEQ ID NO 2
<211> LENGTH: 17
<212> TYPE: PRT
<213> ORGANISM: Artificial
<220> FEATURE:
<221> NAME/KEY: misc_feature
<222> LOCATION: 1..16
<223> OTHER INFORMATION: Synthetic peptide

<400> SEQUENCE: 2

Cys Leu Ala Gly Ala Pro Glu Pro Phe Glu Pro Ala Gln Pro Asp Ala
1               5                   10                  15

Tyr

<210> SEQ ID NO 3
<211> LENGTH: 33
<212> TYPE: PRT
<213> ORGANISM: Artificial
<220> FEATURE:
<221> NAME/KEY: misc_feature
<222> LOCATION: 1..33
<223> OTHER INFORMATION: Synthetic peptide

<400> SEQUENCE: 3

Ala Thr Gln Leu Asp Gly Pro Ala Gly Ala Leu Leu Leu Arg Leu Val
1               5                   10                  15

Gln Leu Ala Gly Ala Pro Glu Pro Phe Glu Pro Ala Gln Pro Asp Ala
```

```
                       20                  25                  30
Tyr

<210> SEQ ID NO 4
<211> LENGTH: 164
<212> TYPE: PRT
<213> ORGANISM: Homo sapiens

<400> SEQUENCE: 4

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140

Arg Leu Val Gln Leu Ala Gly Ala Pro Glu Pro Phe Glu Pro Ala Gln
145                 150                 155                 160

Pro Asp Ala Tyr
```